United States Patent [19]

Foley

[11] 4,039,665

[45] Aug. 2, 1977

[54] METHOD FOR THE ERADICATION OF VENOUS BLEMISHES

[75] Inventor: William T. Foley, New York, N.Y.

[73] Assignee: William T. Foley Foundation, Inc., New York, N.Y.

[21] Appl. No.: 719,695

[22] Filed: Sept. 2, 1976

Related U.S. Application Data

[63] Continuation-in-part of Ser. No. 579,197, May 20, 1975, abandoned.

[51] Int. Cl.² ............................................. A61K 31/725
[52] U.S. Cl. .................................................... 424/183
[58] Field of Search ......................................... 424/183

[56] References Cited

U.S. PATENT DOCUMENTS

| | | | |
|---|---|---|---|
| 3,066,076 | 11/1962 | Monnier | 424/183 X |
| 3,137,624 | 6/1964 | Foley | 424/183 |
| 3,151,025 | 9/1964 | Costello | 424/183 |
| 3,207,665 | 9/1965 | Bucourt | 424/183 |

FOREIGN PATENT DOCUMENTS

| | | | |
|---|---|---|---|
| 464M | 5/1961 | France | 424/183 |
| 3,716M | 11/1965 | France | 424/183 |
| 406,775 | 12/1965 | Netherlands | 424/183 |
| 994,622 | 6/1965 | United Kingdom | 424/183 |
| 1,034,536 | 6/1966 | United Kingdom | 424/183 |
| 1,004,052 | 9/1965 | United Kingdom | 424/183 |

*Primary Examiner*—Dale R. Ore
*Attorney, Agent, or Firm*—Sandoe, Hopgood, Calimafde

[57] ABSTRACT

A method for the eradication of venous blemishes, such as venous "spiders," "sunbursts," telangiectases, venous plexi and groups of dilated venules consists of sclerotherapy employing at least a 20% saline solution with heparin added as a sclerosing agent. The afflicted venules are first partially emptied of blood by gravity and are then completely cleared by forcing small amounts of air through them before they are injected with the sclerosing solution. Chemical burns caused by the caustic effect of extravasated solution on surrounding tissues may be counteracted by injection of water or of a dilute solution of procaine hydrochloride (commonly known as Novocaine) in water.

6 Claims, No Drawings

METHOD FOR THE ERADICATION OF VENOUS BLEMISHES

This application is a continuation-in-part of application Serial No. 579,197, filed May 20, 1975, now abandoned.

This invention relates to a method for the eradication of venous blemishes such as venous "spiders," "sunbursts," telangiectases, venous plexi and goups of dilated venules and the like which are usually observed in the legs.

Venous blemishes are an affliction, not an abnormality. As a cosmetic problem, they create consternation in many women. Many hide their legs under leg make-up or garments, and will not appear in bathing suits. Most women who develop such blemishes do not have a history of phlebitis, varicose veins, venous insufficiency or other stigmata of circulatory problems. The fewer melanophores in the skin, the more apparent these blemishes become. The current vogue of shaving the legs, makes the blemishes more visible. They are also present in men, but fashion has not decreed their interdiction as it has in women. They are found at the ankles, calves and thighs, but rarely elsewhere.

A decade and a half ago, I became interested in the problem of assisting patients with venous insufficiency who had not responded to surgery or to the type of sclerotherapy then employed. Such patients had varices, stasis eczema and ulceration. Surgical ligation, stripping, skin grafting and sclerotherapy had failed.

This problem led to investigation of the medical management of venous insufficiency and the methods of sclerotherapy and compression then employed. The methods of sclerotherapy then employed had several deficiencies. The first of these was the danger of allergic and anaphylactic reaction. The second problem was the development of thrombosis in the injected vein. Such a clot would block the vein, but it often propagated and had been known to embolize. These problems were overcome by the method described in my prior U. S. Pat. No. 3,137,624 dated June 16, 1964, by using a 20% solution of sodium chloride in water with heparin added as described in my patent as a sclerosive solution, and by use of the "empty vein" technique of injection as described in my prior patent. The "empty vein" maneuver was achieved by gravitational drainage of the venous blood from the leg. A tourniquet was applied. The sclerosing solution was then injected into the empty vein. This produced an inflammation of the endothelial lining. The inflamed lining became adherent to itself. The lumen became obliterated.

Success with the above method, particularly for the therapy of varicose veins, led patients to seek treatment for venous blemishes in order to improve the cosmetic appearance of their legs. The simple injection of a sclerosing solution into these lesions as described in my prior patent posed many problems. First of all, the venules that comprise the conglomeration are so tiny that standard-sized hollow needles are too large to enter the venules. This problem was solved by the development of 30 disposable needles. With the help of a magnifying lens (loop) some venule within the area of a blemish can usually be found which can be entered by the 30 needle.

The second problem was the development of ugly brown stains after injection of the sclerosing solution due to the fact that blood was hemolyzed by the hypertonic saline solution. Hemosiderin was formed and made the stains. To prevent this, I developed a method to clear the blood completely from the area of the lesion by first partially removing the blood therefrom by gravity, as by elevating the leg above the level of the heart, and then by immediate injection of minute amounts of air into the area prior to injection of the sclerosing solution. In the interval while the lesion is bloodless, the injection of the solution is made. It will be understoood that because of the minute nature of the venules, it is not possible to rely on gravity alone to clear the blood completely from the lesion. Complete clearing is required if stains are to be avoided. Preferably, the sclerosing solution is that described in my prior patent, i.e. a solution of sodium chloride in water.

The strength of the sodium chloride solution may vary from 20% (20 grams of sodium chloride in sufficient water to make 100 cc. of solution) to a completely saturated solution of approximately 35% (35 grams of sodium chloride in sufficient water to make 100 cc. of solution). I prefer, however, to use a saturated or nearly saturated solution. I also prefer to use distilled water in the solution.

To such solution is added sufficient heparin (sometimes referred to as heparin sodium) to provide the desired anticoagulant activity, namely, a minimum of 100 units of anticoagulant activity per 100 cc. of solution. Heparin as available commercially is standardized to possess not less than 100 units of anticoagulant activity per milligram of dry material. I therefore add a minimum of 1 mg. of heparin per 100 cc. of solution, but I prefer to add 3 to 5 mg. of heparin per 100 cc. of solution to insure adequate anticoagulant activity. However, additional heparin may be added if desired, for as much as 10,000 units of anticoagulant activity per 100 cc. of solution may be tolerated with safety.

A third problem was the development of chemical burns. These are caused by the caustic effect of the sclerosing solution on the tissues if the sclerosing solution is injected outside of a venule, or if any of the venules within the area of the lesion break. To counteract this, the extravasated solution in the area of the lesion must be immediately diluted at least to 0.9% of NaCl by injecting at least 20 times as much water as the estimated amount of transversate. Preferably, a 1% solution of procaine hydrochloride in water is used for it has been found that it is more effective than plain water. It gives anaesthesia as well as dilution.

The following procedure exemplifies the therapy, according to the present invention, for the eradication of venous blemishes as above described.

The blemish is first carefully examined under magnification. A venule within the area of the lesion is selected that has a caliber large enough to allow entrance of a 30 needle. The leg is then positioned in such a way that the lesion is higher than the heart and positioned so that the injections can be given vertically. The elevation above the heart is to assist the gravitational flow of the blood out of the area. The vertical injection is to insure the propulsion of air into the lesion prior to injection of the solution. 4 cc of the sclerosing solution is sucked into a syringe. One-half cc. of air is added. With the syringe held in inverted position, i.e. with the needle at the top so that the air is trapped in the upper end of the syringe, the selected venule is entered. The syringe is then operated to inject the air rapidly into the selected venule. If the needle is well inside the venule, the blood can be seen to rush out of the area of the lesion as the air spreads through the area. An area of as much as 5 cm.

in diameter will blanch. The sclerosing solution is then injected slowly into said venule at a rate of approximately 1 cc. per minute to fill the emptied venules of the area. If the venule breaks, or if the sclerosing solution enters the surrounding tissue in any manner, the procaine solution may be injected into the area at once.

The therapy may be repeated as desired. Only rarely, however, is it advisable to treat at one time areas that require more than a total injection of 5 cc. More extensive treatments covering wider area are feasible at later times.

What is claimed is:

1. The method of treating venous blemishes such as venous spiders, sun-bursts, telangiectases, venous plexi, and groups of dilated venules which comprises partially removing the blood from the venules of the afflicted area by gravity, then injecting air into a selected venule within the area to clear the blood completely from the venules of the afflicted area, and then injecting a sclerosing solution into said selected venule to fill the cleared venules of the area, said sclerosing solution comprising at least 20% sodium chloride in water with heparin added.

2. The method as claimed in claim 1 in which said sclerosing solution comprises at least 1 mg. of heparin per 100 cc. of solution.

3. The method as claimed in claim 1 in which the sclerosing solution is injected slowly at a rate of approximately 1 cc. per minute.

4. The method as claimed in claim 1 which includes the further step of diluting the solution within the area by injecting water into the area.

5. The method as claimed in claim 4 in which the water contains 1% of procaine hydrochloride.

6. The method as claimed in claim 4 in which the quantity of water injected is at least 20 times the quantity of the extravasated sclerosing solution in the area.

* * * * *